United States Patent
Oepping et al.

(10) Patent No.: US 11,090,020 B2
(45) Date of Patent: Aug. 17, 2021

(54) ADJUSTING A COLLIMATOR OF AN X-RAY SOURCE

(71) Applicant: Siemens Healthcare GmbH, Erlangen (DE)

(72) Inventors: Susanne Oepping, Erlangen (DE); Ralf Nanke, Neunkirchen am Brand (DE); Michael Fuhrmann, Herzogenaurach (DE); Birgi Tamersoy, Erlangen (DE); Yao-jen Chang, Princeton, NJ (US); Terrence Chen, Princeton, NJ (US)

(73) Assignee: SIEMENS HEALTHCARE GMBH, Erlangen (DE)

( * ) Notice: Subject to any disclaimer, the term of this patent is extended or adjusted under 35 U.S.C. 154(b) by 0 days.

(21) Appl. No.: 16/357,533

(22) Filed: Mar. 19, 2019

(65) Prior Publication Data
US 2019/0290236 A1 Sep. 26, 2019

(30) Foreign Application Priority Data
Mar. 26, 2018 (EP) ..................................... 18163993

(51) Int. Cl.
*A61B 6/06* (2006.01)
*A61B 6/08* (2006.01)
*A61B 6/00* (2006.01)
*G21K 1/04* (2006.01)

(52) U.S. Cl.
CPC ............... *A61B 6/545* (2013.01); *A61B 6/06* (2013.01); *A61B 6/08* (2013.01); *A61B 6/4405* (2013.01); *A61B 6/4452* (2013.01); *A61B 6/46* (2013.01); *A61B 6/587* (2013.01); *A61B 6/588* (2013.01); *A61B 6/547* (2013.01); *G21K 1/04* (2013.01)

(58) Field of Classification Search
None
See application file for complete search history.

(56) References Cited

U.S. PATENT DOCUMENTS

| 6,206,566 | B1 * | 3/2001 | Schuetz | A61B 6/547 378/205 |
| 6,379,041 | B1 * | 4/2002 | Schuetz | A61B 6/547 378/205 |
| 6,435,715 | B1 * | 8/2002 | Betz | A61B 6/4458 378/197 |

(Continued)

FOREIGN PATENT DOCUMENTS

| DE | 102009013572 A1 | 9/2010 |
| EP | 2767236 A1 | 8/2014 |

OTHER PUBLICATIONS

European Search Report with Patent Application No. 18163993.1 dated Sep. 18, 2018.

*Primary Examiner* — Thomas R Artman
(74) *Attorney, Agent, or Firm* — Harness, Dickey & Pierce, P.L.C.

(57) ABSTRACT

A method is disclosed for adjusting a collimator of an X-ray source. In an embodiment, the method includes detecting an arrangement of an X-ray detector with respect to the X-ray source; automatically determining an adjustment for the collimator based on the detected position of the X-ray detector with respect to the X-ray source; and automatically adjusting the collimator based on the determined adjustment for the collimator. An X-ray device and computer readable medium are also disclosed.

16 Claims, 2 Drawing Sheets

(56) References Cited

U.S. PATENT DOCUMENTS

| | | | | |
|---|---|---|---|---|
| 7,010,080 | B2* | 3/2006 | Mitschke | A61B 6/12 378/15 |
| 8,303,181 | B2* | 11/2012 | Sukovic | A61B 6/547 378/197 |
| 9,566,040 | B2* | 2/2017 | Hu | A61B 6/5205 |
| 9,642,584 | B2* | 5/2017 | Niebler | A61B 6/547 |
| 9,895,131 | B2 | 2/2018 | Chang et al. | |
| 9,904,998 | B2* | 2/2018 | Jockel | A61B 6/08 |
| 10,076,293 | B2* | 9/2018 | Sehnert | A61B 6/06 |
| 10,463,323 | B2* | 11/2019 | Maack | A61B 6/4233 |
| 10,478,149 | B2* | 11/2019 | Tamersoy | A61B 6/4458 |
| 10,507,002 | B2* | 12/2019 | Singh | A61B 6/42 |
| 10,542,958 | B2* | 1/2020 | Merckx | A61B 6/545 |
| 10,568,602 | B2* | 2/2020 | Tkaczyk | A61B 6/04 |
| 2004/0258210 | A1* | 12/2004 | Ritter | A61B 5/107 378/198 |
| 2005/0004454 | A1* | 1/2005 | Mitschke | A61B 6/547 600/427 |
| 2005/0054915 | A1* | 3/2005 | Sukovic | A61B 6/032 600/424 |
| 2010/0239070 | A1 | 9/2010 | Mohr | |
| 2012/0155615 | A1 | 6/2012 | Liu | |
| 2013/0083894 | A1* | 4/2013 | Niebler | A61B 6/4441 378/62 |
| 2015/0223767 | A1* | 8/2015 | Sehnert | A61B 6/4411 378/42 |
| 2015/0228071 | A1* | 8/2015 | Jockel | H04N 13/204 382/132 |
| 2015/0327821 | A1* | 11/2015 | Hu | A61B 5/0077 378/62 |
| 2015/0374314 | A1 | 12/2015 | Maack et al. | |
| 2016/0220223 | A1 | 8/2016 | Kim et al. | |
| 2016/0331334 | A1* | 11/2016 | Imamura | A61B 6/4283 |
| 2017/0055925 | A1 | 3/2017 | Lee et al. | |
| 2017/0112460 | A1* | 4/2017 | Merckx | A61B 6/545 |
| 2017/0119338 | A1* | 5/2017 | Merckx | A61B 6/08 |
| 2017/0303879 | A1* | 10/2017 | Maack | A61B 6/4452 |
| 2018/0235566 | A1 | 8/2018 | Tamersoy et al. | |
| 2018/0296177 | A1 | 10/2018 | Chang et al. | |
| 2018/0338742 | A1* | 11/2018 | Singh | A61B 6/587 |
| 2019/0069871 | A1* | 3/2019 | Tkaczyk | A61B 6/04 |
| 2019/0290236 | A1* | 9/2019 | Oepping | A61B 6/588 |
| 2020/0058389 | A1* | 2/2020 | Saalbach | A61B 5/0077 |

* cited by examiner

ADJUSTING A COLLIMATOR OF AN X-RAY SOURCE

PRIORITY STATEMENT

The present application hereby claims priority under 35 U.S.C. § 119 to European patent application number EP 18163993.1 filed Mar. 26, 2018, the entire contents of which are hereby incorporated herein by reference.

FIELD

Embodiments of the invention generally relate to a method for adjusting a collimator of an X-ray source and to a corresponding X-ray device. Furthermore, embodiments of the invention generally relate to a corresponding computer program product and a computer readable media are provided.

BACKGROUND

X-ray imaging is widely used in medical examination. An X-ray imaging device may comprise a fixed X-ray detector such that the position and size of the X-ray detector as well as the distance between the X-ray radiation source and the X-ray detector are well defined within the X-ray imaging device. The X-ray imaging device may be configured such that the size of a light field irradiated by the X-ray source matches to an active field of the X-ray detector. However, X-ray imaging devices may also utilise mobile X-ray detectors to allow free exposures. The mobile X-ray detector may be arranged as required with respect to an examination object and the radiation X-ray source may be moved freely to focus on a region of interest of the examination object, for example a body part of a patient to be examined.

Due to the free arrangement of the X-ray detector and the X-ray source, an area irradiated by the X-ray source (light field size) may be larger or may extend beyond an active field of the mobile X-ray detector. This may lead to an increased X-ray dose for the patient. An operator of the X-ray imaging device may align the X-ray source and may adjust a collimator of the X-ray source such that the collimated field is restricted to the active area of the X-ray detector. However, this demand may be difficult to fulfil and may require several iterations of manual adjustment, which may be time-consuming.

SUMMARY

Accordingly, the inventors have discovered that a need exists to improve X-ray imaging devices which utilise a mobile X-ray detector.

This need is met by the features of the independent claims. The dependent claims describe further aspects.

According to a first embodiment, a method for adjusting a collimator of an X-ray source is provided. According to the method, an arrangement of an X-ray detector with respect to the X-ray source is detected. Based on the detected position of the X-ray detector with respect to the X-ray source, an adjustment for the collimator is automatically determined. Based on the determined adjustment for the collimator, the collimator is automatically adjusted.

According to a another embodiment, a method for adjusting a collimator of an X-ray source is provided. The method comprise:

detecting an arrangement of an X-ray detector with respect to the X-ray source to determine a position of the X-ray detector detected with respect to the X-ray source;

automatically determining an adjustment for the collimator based on the position of the X-ray detector determined with respect to the X-ray source; and automatically adjusting the collimator based on the adjustment determined for the collimator.

According to another embodiment, an X-ray device is provided. The X-ray device comprises an X-ray source comprising a collimator, a capturing device configured to detect an arrangement of an X-ray detector with respect to the X-ray source, and a processing device. The capturing device may comprise for example a camera, in particular a 3-D digital camera. The processing device may comprise for example a digital processing device like a controller or a central processing unit (CPU) including memory and input and output interfaces for receiving information from for example the capturing device, a graphical user interface, and for providing information to actuators for adjusting the collimator. The processing device is configured to determine an adjustment for the collimator based on the detected position of the X-ray detector with respect to the X-ray source, and to adjust the collimator based on the determined adjustment for the collimator.

According to another embodiment, an X-ray device is provided. The X-ray device, comprises:

an X-ray source including a collimator;
an X-ray detector; and
at least one processor configured to
detect an arrangement of the X-ray detector with respect to the X-ray source;
automatically determine an adjustment for the collimator based on a position of the X-ray detector determined with respect to the X-ray source; and
automatically adjust the collimator based on the adjustment determined for the collimator.

A further embodiment of the present invention relates to a computer program product comprising a computer program. The computer program is loadable into a memory of a processing device of an X-ray device. The computer program includes program code sections to cause the processing device to execute an embodiment of the above-described method when the computer program is executed in the processing device. The computer program product may comprise other elements apart from the computer program. These other elements may be hardware, for example a memory device, on which the computer program is stored, a hardware key for using the computer program and the like, and/or software, for example a documentation or a software key for using the computer program.

Furthermore, according to another embodiment, a computer readable media is provided which includes computer executable instructions for performing an embodiment of the above-described method. The computer readable media may comprise for example a DVD, a magnetic tape, a hard disk or an USB stick, on which electronically readable control information, in particular software, is stored. Upon reading this control information from the computer readable media into a processing device of an X-ray device, the above-described method may be performed by the processing device.

BRIEF DESCRIPTION OF THE DRAWINGS

The invention will be described below with reference to the accompanying drawings using example embodiments.

The illustrations in the figures are schematic and highly simplified and are not necessarily to scale.

DETAILED DESCRIPTION OF THE EXAMPLE EMBODIMENTS

Figure 1:
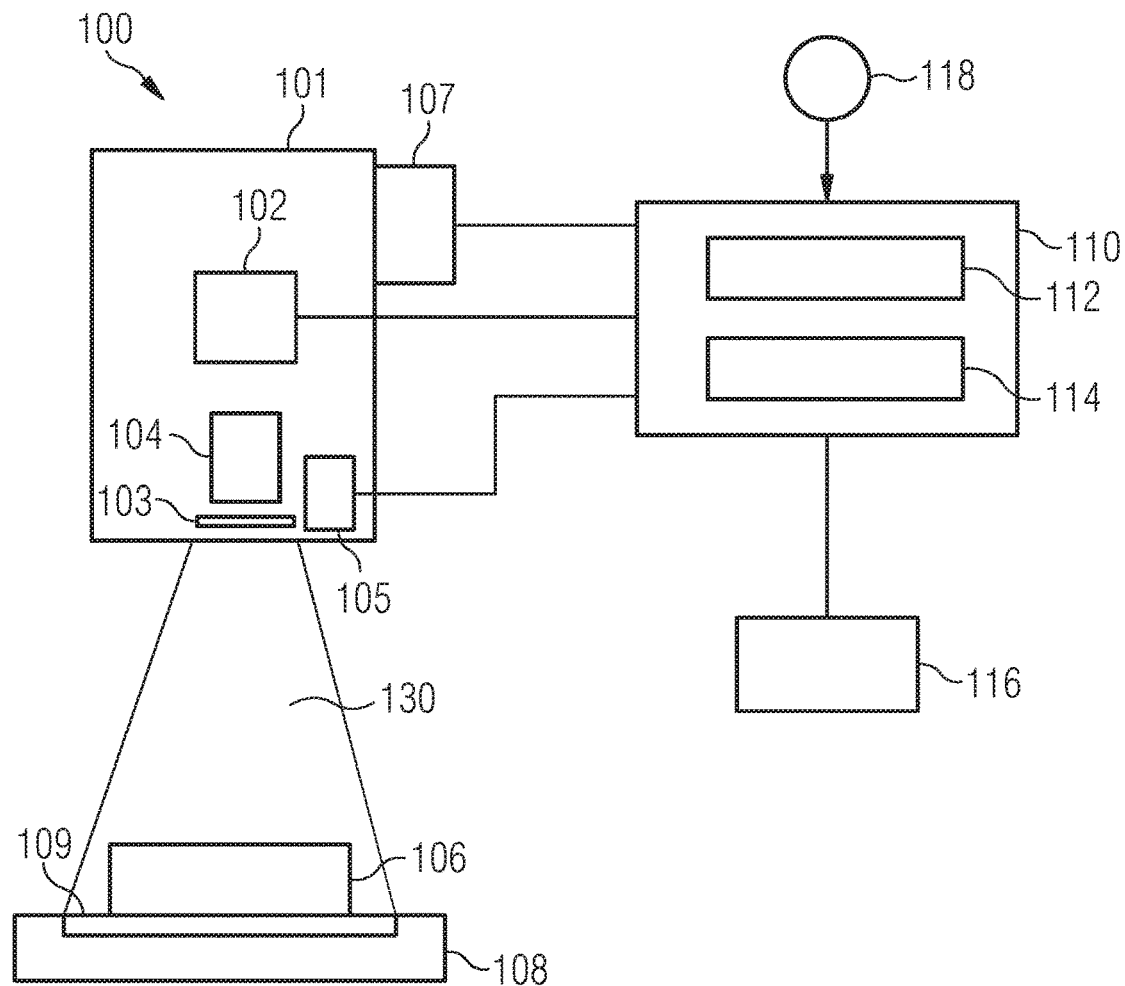
FIG. 1 shows schematically a medical X-ray imaging device according to an embodiment of the invention.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/ hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

Most of the aforementioned components, in particular the identification unit, can be implemented in full or in part in the form of software modules in a processor of a suitable control device or of a processing system. An implementation largely in software has the advantage that even control devices and/or processing systems already in use can be easily upgraded by a software update in order to work in the manner according to at least one embodiment of the invention.

According to a first embodiment, a method for adjusting a collimator of an X-ray source is provided. According to the method, an arrangement of an X-ray detector with respect to the X-ray source is detected. Based on the detected position of the X-ray detector with respect to the X-ray source, an adjustment for the collimator is automatically determined. Based on the determined adjustment for the collimator, the collimator is automatically adjusted.

A camera, for example a digital camera, in particular a digital 3-D camera, may be used to detect the arrangement of the X-ray detector. The X-ray detector may comprise a mobile X-ray detector allowing free exposure arrangement of the X-ray detector. A position of the camera with respect to the X-ray source may be fixed. As an alternative, the camera may additionally detect the position and orientation of the X-ray source such that the arrangement of the X-ray detector with respect to the X-ray source may be determined. For example, an image showing the X-ray detector and the X-ray source may be captured and based on the captured image, a distance between the X-ray detector and the X-ray source, an orientation of the X-ray detector with respect to the X-ray source, and/or a size of an active field of the X-ray detector may be automatically determined, for example by a processing device which performs an image processing.

Thus, parameters like X-ray detector position and orientation, distance between the X-ray detector and the X-ray source, a size and an orientation of the collimator may be determined in a three-dimensional coordinate system or relative to the camera. Based on these parameters, the active area of the mobile X-ray detector and the area irradiated by the collimator (light field) may be compared and the setup may be changed automatically, in particular adjusting the collimator. For example, the maximum opening of the collimator may be limited to the borders of the mobile X-ray detector such that an X-ray dose irradiated on the patient may be decreased.

According to an example embodiment, automatically adjusting the collimator may comprise automatically adjusting a height or automatically adjusting a width of a light field of the collimator. Further, a rotation of the light field of the collimator may automatically be adjusted. This may limit the maximum opening of the collimator to the borders of the mobile X-ray detector. Further, free arrangement of the mobile X-ray detector may be supported, for example by rotating the light field of the collimator. Further, when the distance between the X-ray source and the mobile X-ray detector is changed, the collimator size may be adapted so that the collimation of the light field remains the same. Adjusting the width, height and/or rotation of the light field of the collimator may be accomplished by adjusting corresponding blades which may be driven by actuators controlled by a processing device.

In another example embodiment, the arrangement of the X-ray source may be adjustable. For detecting the arrangement of the X-ray detector with respect to the X-ray source, the position of the X-ray detector may be detected and an adjustment for the X-ray source may be automatically determined based on the detected position of the X-ray detector. A position of the X-ray source is automatically adjusted based on this determined adjustment for the X-ray source. The position of the X-ray detector as well as the position of the X-ray source may be determined based on an image captured by a camera, in particular a 3-D camera.

For example, based on the detected arrangement of the X-ray detector with respect to the X-ray source, a processing device may determine that this setup has to be changed. If the position and orientation of the X-ray detector have to be changed, the X-ray source may be moved to a position where an area irradiated by the X-ray source (light field) covers the active area of the X-ray detector. Next, the collimator may be adjusted such that the area irradiated by the X-ray source (light field) does not extend beyond the active area of the X-ray detector.

According to another example embodiment, a warning indicating that an optimal adjustment of the collimator cannot be achieved with the detected arrangement of the X-ray detector with respect to the X-ray source is output to an operator. The operator may then consider to rearrange the X-ray detector in combination with the object to be examined, and the above-described method may be repeated for automatically adjusting the collimator.

According to another embodiment, an X-ray device is provided. The X-ray device comprises an X-ray source comprising a collimator, a capturing device configured to detect an arrangement of an X-ray detector with respect to the X-ray source, and a processing device. The capturing device may comprise for example a camera, in particular a 3-D digital camera. The processing device may comprise for example a digital processing device like a controller or a central processing unit (CPU) including memory and input and output interfaces for receiving information from for example the capturing device, a graphical user interface, and for providing information to actuators for adjusting the collimator. The processing device is configured to determine an adjustment for the collimator based on the detected position of the X-ray detector with respect to the X-ray source, and to adjust the collimator based on the determined adjustment for the collimator.

The X-ray device may be configured to perform the above-described method in an embodiment.

A further embodiment of the present invention relates to a computer program product comprising a computer program. The computer program is loadable into a memory of a processing device of an X-ray device. The computer program includes program code sections to cause the processing device to execute an embodiment of the above-described method when the computer program is executed in the processing device. The computer program product may comprise other elements apart from the computer program. These other elements may be hardware, for example a memory device, on which the computer program is stored, a hardware key for using the computer program and the like, and/or software, for example a documentation or a software key for using the computer program.

Furthermore, according to another embodiment, a computer readable media is provided which includes computer executable instructions for performing an embodiment of the above-described method. The computer readable media may comprise for example a DVD, a magnetic tape, a hard disk or an USB stick, on which electronically readable control information, in particular software, is stored. Upon reading this control information from the computer readable media into a processing device of an X-ray device, the above-described method may be performed by the processing device.

It is to be understood that the features mentioned above and features yet to be explained below may be used not only in the respective combinations indicated, but also in other combinations or in isolation without departing from the scope of the present invention. Features of the above-mentioned aspects and examples and the embodiments described below may be combined with each other unless specifically mentioned otherwise.

In the following, embodiments of the invention will be described in detail with reference to the accompanying drawings. It is to be understood that the following description of embodiments is not to be taken in a limiting sense. The scope of the invention is not intended to be limited by the embodiments described herein or by the drawings, which are to be illustrative only.

The drawings are to be regarded as being schematic representations, and elements illustrated in the drawings are not necessarily shown to scale. Rather, the various elements are represented such that their function and general purpose becomes apparent to a person skilled in the art. Any connection or coupling between functional blocks, devices, components of physical or functional units shown in the drawings and described herein may also be implemented by an indirect connection or coupling. Any coupling between components may be established over a wired or wireless connection. Functional blocks may be implemented in hardware, software, firmware, or a combination thereof.

Same reference signs in the various drawings refer to similar or identical components.

FIG. 1 shows schematically an X-ray imaging device 100. The X-ray imaging device 100 comprises an X-ray source 101 comprising a radiation source 102, for example an X-ray tube, configured to emit an X-ray beam through a collimator 104. The collimator 104 is arranged to collimate the X-ray beam. The collimator 104 may be configured to restrict a spatial extent of the X-ray beam in one or more directions perpendicular to a direction of propagation of the beam. The X-ray beam passing through the collimator 104 is further passing through an collimator adjustment system 103 of the collimator 104. The collimator adjustment system 103 may comprise movable blades for adjusting a light field which is irradiated by the X-ray beam passing through the collimator 104. The X-ray source 101 comprises furthermore an actuator 105 which may be coupled to the collimator adjustment system 103 for moving the blades based on control information provided to the actuator 105.

The X-ray source 101 may comprise a further actuator 107 for adjusting a position and an orientation of the X-ray source 101. Furthermore, the X-ray source 101 may comprise further components, for example a further actuator for moving the radiation source 102 with respect to the collimator 104.

An X-ray beam 130 generated by the X-ray source 101 may be directed to an object 106 to be imaged. The object 106 may be located on or near an imaging platform 108. The imaging platform 108 may comprise or constitute an X-ray detector arranged to detect X-ray radiation emitted from the radiation source 102. For example, the imaging platform 108 may be arranged to receive a cassette containing a radiographic or photographic film reactive to the radiation emitted from the radiation source 102. In another example, the imaging platform 108 may comprise an electronic flat panel X-ray detector. The imaging platform 108 may have an active area 109 which is responsive to the incoming X-ray radiation, whereas a remaining part of the surface of the imaging platform 108, for example a frame surrounding the active area 109, may not be responsive to the incoming X-ray radiation.

The X-ray imaging device 100 may comprise a processing device 110 for controlling the radiation source 102 and the actuators 105, 107. For example, the processing device 110 may control a position and/or an orientation of the X-ray source 101 to control a position from which radiation is emitted from the radiation source 102 and/or one or more settings of the collimator 104. For example, the processing device 110 may be configured to generate control signals for controlling drive motors or other electromechanical drives of the actuators 105, 107 connected to the X-ray source 101 and the collimator 104 to control the position, orientation, and/or extent of the emitted X-ray beam 130.

The processing device 110 may be implemented using hardware and/or software. For example, the processing device 110 may comprise a processor 112 programmed to perform the functions of the processing device 110. The control device 110 may further include a memory 114 arranged to store data, for example program code executable by the processor 112 to perform the functions of the processing device 110. The program code may be loaded into the memory 114 from a computer readable media, for example a DVD 118, an USB stick or via a data communication network. The program code may in particular be configured to perform a method described herein with reference to FIG. 4.

Furthermore, the imaging device 100 may comprise a capturing device 116 configured to detect an arrangement of the imaging platform 108 with respect to the X-ray source 101. The capturing device 116 may comprise for example a camera, for example an optical digital camera, in particular a 3-D camera. The camera may be configured t provide one or more color channels or may be configured to provide a greyscale image. The 3-D camera may be configured to provide one or more color or greyscale channels and one or more depth channels. In some embodiments, the imaging device 100 may comprise one or more (not shown) interfaces for receiving a connection to a camera not permanently connected to the imaging device 100.

The capturing device may be mechanically connected to the X-ray source 101 so that the capturing device moves together with the X-ray source 101. Accordingly, images generated by the capturing device will include an area that will be irradiated by the radiation source 102 wherever the X-ray source 101 is located. As an alternative, as shown in FIG. 1, the capturing device 116 may be arranged spaced apart from the X-ray source 101 and the imaging platform 108, but such that an image captured by the capturing device 116 shows at least the imaging platform 108 and optionally also the X-ray source 101. However, a relative arrangement between the capturing device 116 and the X-ray source 101 may be known to the processing device 110 based on a control of the actuator 107. Additionally or as an alternative, the image captured by the capturing device 116 may show the arrangement of the imaging platform 108 in relation to the X-ray source 101.

Figure 2:
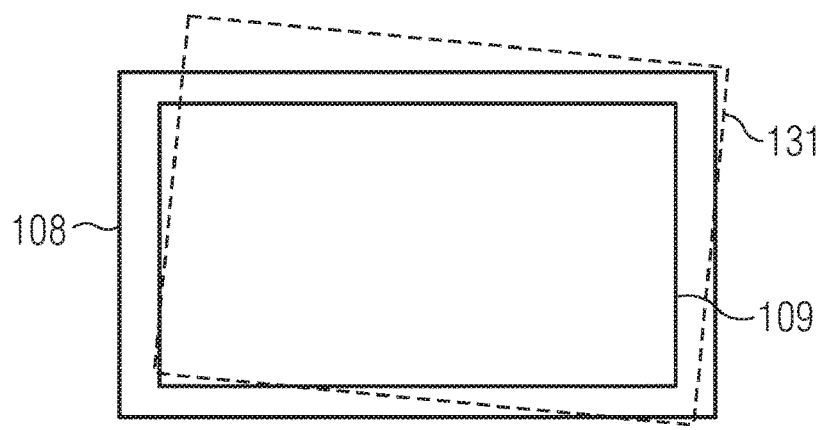
FIG. 2 shows schematically a light field of a collimator relative to an active area of an X-ray detector.
Figure 3:
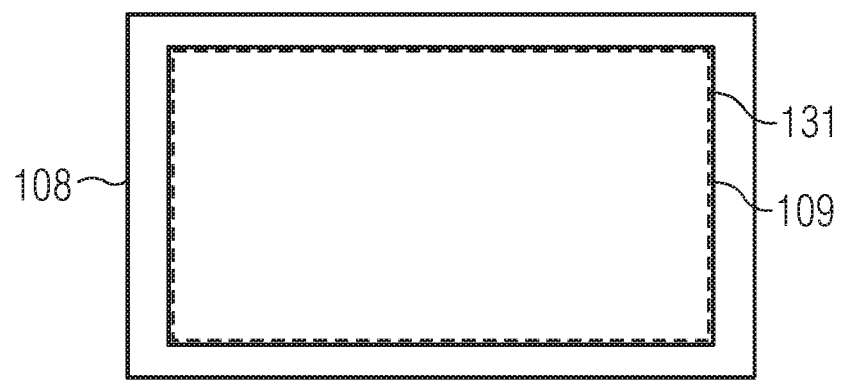
FIG. 3 shows schematically an adjusted light field of a collimator relative to an active area of an X-ray detector.

The imaging platform 108 is movable and may be freely arranged as required and appropriate for taking X-ray images of an object to be examined, for example of a body part like an arm or leg of a patient. As the imaging platform 108 is freely movable, the active area 109 of the imaging platform 108 may not match to an area irradiated by the X-ray beam 130. The area irradiated by the X-ray beam 130 will be called in the following light field of the X-ray source 101. The light field of the X-ray source 101 may be defined by its outline or contour, for example by a width, a height and an orientation. The outline of the light field may be modified by rearranging the X-ray source 101, for example controlled by the processing device 110 using the actuator 107. However, due to mechanical restrictions, for example a distance between the X-ray source 101 and the imaging platform 108, or due to X-ray radiation restrictions, for example a required X-ray intensity, a matching of the light field of the X-ray beam 130 to the active area 109 of the imaging platform 108 may not be possible. Further, the width-to-height-ratio of the active area 109 and the light field of the X-ray beam 130 may not be matching. FIG. 2 shows an example of an active area 109 of the imaging platform 108 which does not match to the light field 131 of the X-ray beam 130. When the light field 131 does not match the active area 109, some significant areas may not be irradiated resulting in an incomplete X-ray image, and some not significant areas may be irradiated resulting in an unnecessary high X-ray dose for the patient. An aligned light field 131 matching to the active area 109 as shown in FIG. 3 may mitigate such drawbacks.

Figure 4:
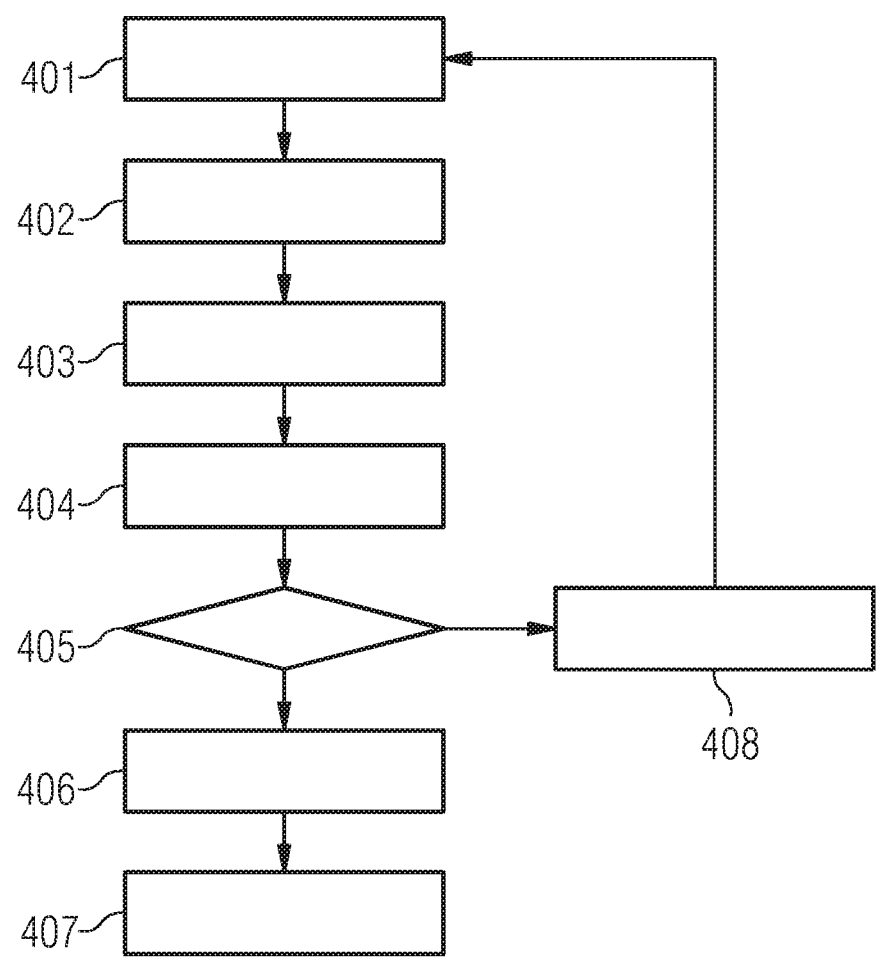
FIG. 4 shows a workflow diagram illustrating a method according to an embodiment of the invention.

In connection with FIG. 4, method steps will be described in the following which are executed by the processing device 110 to align the light field 131 to the active area 109 of the freely movable imaging platform 108. The method comprises method steps 401 to 408, wherein some method steps may be optional, in particular steps 402, 403, 405, 407 and 408.

Steps 401 to 403 illustrate an example of detecting an arrangement of the imaging platform (X-ray detector) 108 with respect to the X-ray source 101. For example, in step 401 an image may be captured with the capturing device 116. The image may comprise at least an image of the imaging platform 108, in particular the active area 109 which is sensitive to the X-ray beam 130. The X-ray source 101 may be movable under control of the actuator 107. For example a position and orientation of the X-ray source 101 may be configurable and controllable via the actuator 107 by the processing device 110. If the position of the capturing device 116 and the current position of the X-ray source 101 is known to the processing device 110, the arrangement of the imaging platform 108 with respect to the X-ray source 101 may be determined based on the image from the capturing device 116 which shows the imaging platform 108. However, as an alternative, the image captured by the capturing device 116 may show the imaging platform 108 and the X-ray source 101 such that the relative position of the imaging platform 108 with respect to the X-ray source 101 may be determined based on the image by image processing performed by the processing device 110. In particular, the processing device 110 may automatically compute based on the image captured by the capturing device 116 a distance between the imaging platform 108 and the X-ray source 101, an orientation of the imaging platform 108 with respect to the X-ray source 101 and/or a size of the active field 109 of the imaging platform 108.

In step 402, an adjustment for the X-ray source 101 may be determined by the processing device 110 based on the detected position of the imaging platform 108 with respect to the current position of the X-ray source 101. Based on the determined adjustment for the X-ray source 101, actuator 107 may be controlled by the processing device 110 to rearrange the X-ray source 101 according to the determined adjustment (step 403). As a result, the X-ray beam 130 from the X-ray source 101 should be at least coarsely directed to the imaging platform 108. At this stage, the light field 131 of the X-ray beam 130 irradiated by the X-ray source 101 may be arranged with respect to the imaging platform 108 as shown in FIG. 2. Furthermore, at this stage, also the current arrangement of the imaging platform 108 with respect to the X-ray source 101 is known to the processing device 110.

In step 404 the processing device 110 determines an adjustment for the collimator 104 based on the detected position of the imaging platform 108 with respect to the X-ray source 101. This adjustment for the collimator 104 may comprise for example an adjustment of a height of the light field 131, an adjustment of a width of the light field 131 and/or an adjustment of rotation or orientation of the light field 131.

There may be arrangements of the imaging platform 108 with respect to the X-ray source 101 which do not allow to align the light field 131 to the active area 109. This may be determined in step 405, and in case an aligned or optimal adjustment of the collimator cannot be achieved with the detected arrangement of the imaging platform 108 with respect to the X-ray source 101, a corresponding warning may be output in step 408 to an operator of the imaging device 100. In response to this warning, the operator may have to rearrange the imaging platform 108 and the object 106 to be examined, and the method may be continued in step 401.

In case in step 405 is determined that an aligned or optimal adjustment of the collimator 104 can be achieved for the present arrangement of the imaging platform 108 with respect to the X-ray source 101, the collimator adjustment system 103 may be adjusted based on the determined adjustment for the collimator 104 in step 406. As a result, the light field 131 emitted by the X-ray source 101 and restricted and collimated by the collimator 104 and the collimator adjustment system 103 may be aligned to the active area 109 of the imaging platform 108 as shown in FIG. 3. Finally, in step 407, the processing device 110 may control the X-ray source 101 to emit the X-ray beam 130 such that an X-ray image of the object 106 may be taken by the imaging platform 108.

To sum up, the collimation size is automatically adjusted according to the active area 109 of the mobile imaging platform 108 for free exposures. Thus, the maximum opening of the collimator 104 is limited to the borders of the active area 109 of the mobile imaging platform 108. This may reduce the dose for the patient as optimal collimation is possible according to the size of the active area 109 of the imaging platform 108. When the distance between the X-ray source 101 and the imaging platform 108 is changed, the collimator size may be adapted so that the collimation of the object to be examined remains the same.

While the invention has been illustrated and described in detail with respect to preferred embodiments, the invention is not limited to the disclosed examples. Other variations may be deducted by those skilled in the art without leaving the scope of protection of the claimed invention.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

REFERENCE LIST

100 imaging device
101 x-ray source
102 radiation source
103 collimator adjustment system
104 collimator
105,107 actuator
106 object
108 imaging platform/X-ray detector
109 active area (of imaging platform)
110 processing device
112 processor
114 memory
116 capturing device
118 computer readable media
130 x-ray beam
131 light field (irradiated by x-ray beam)
401 detect position of imaging platform/x-ray detector
402 determine adjustment for x-ray source
403 adjust position of x-ray source
404 determine adjustment for collimator
405 determine, if collimator adjustment con be achieved
406 adjust collimator
407 take x-ray image
408 output warning

What is claimed is:

1. A method for adjusting a collimator of an X-ray source having a radiation source therein, comprising:
   detecting, via a 3D camera, an arrangement of an X-ray detector with respect to the X-ray source;
   automatically determining an adjustment for the collimator based on a position of the X-ray detector determined with respect to the X-ray source;
   moving the radiation source with respect to the collimator; and
   automatically adjusting the collimator based on the adjustment determined for the collimator, wherein the 3D camera is mechanically connected to the X-ray source and is configured to move together with the X-ray source,
wherein an image generated by the 3D camera includes an irradiation area of the X-ray source, and
wherein the image generated by the 3D camera includes the X-ray detector.

2. The method of claim 1, wherein the X-ray detector comprises a mobile X-ray detector to allow a free exposure arrangement of the X-ray detector.

3. The method of claim 2, wherein the automatically adjusting of the collimator comprises at least one of:
automatically adjusting a height of a light field of the collimator,
automatically adjusting a width of the light field of the collimator, and
automatically adjusting a rotation of the light field of the collimator.

4. The method of claim 1, wherein the automatically adjusting of the collimator comprises at least one of:
automatically adjusting a height of a light field of the collimator,
automatically adjusting a width of the light field of the collimator, and
automatically adjusting a rotation of the light field of the collimator.

5. The method of claim 1, wherein the detecting of the arrangement of the X-ray detector with respect to the X-ray source comprises detecting a position of the X-ray detector, and wherein
an adjustment for the X-ray source is automatically determined based on the position of the X-ray detector detected, and
a position of the X-ray source is automatically adjusted based on the adjustment for the X-ray source determined.

6. The method of claim 1, further comprising:
outputting a warning indicating when an optimal adjustment of the collimator cannot be achieved with arrangement of the X-ray detector detected with respect to the X-ray source.

7. A non-transitory computer program product storing a computer program, the computer program being loadable into a memory of a processing device of an X-ray device, and including program code sections to cause the processing device to execute the method of claim 1 when the computer program is executed in the processing device.

8. A non-transitory computer readable media storing computer executable instructions for, when executed by a processor, perform the method of claim 1.

9. A method for adjusting a collimator of an X-ray source, comprising:
detecting, via a 3D camera, an arrangement of an X-ray detector with respect to the X-ray source to determine a position of the X-ray detector detected with respect to the X-ray source;
automatically determining an adjustment for the collimator based on the position of the X-ray detector determined with respect to the X-ray source; and
automatically adjusting the collimator based on the adjustment determined for the collimator,
wherein the detecting of the arrangement of the X-ray detector with respect to the X-ray source comprises;
capturing an image comprising the X-ray detector and the X-ray source,
automatically computing, based on the image captured, at least one of:
a distance between the X-ray detector and the X-ray source, and
an orientation of the X-ray detector with respect to the X-ray source.

10. The method of claim 9, wherein the X-ray detector comprises a mobile X-ray detector to allow a free exposure arrangement of the X-ray detector.

11. The method of claim 10, wherein the automatically adjusting of the collimator comprises at least one of:
automatically adjusting a height of a light field of the collimator, and
automatically adjusting a width of the light field of the collimator.

12. The method of claim 9, further comprising:
outputting a warning indicating when an optimal adjustment of the collimator cannot be achieved with arrangement of the X-ray detector detected with respect to the X-ray source.

13. A non-transitory computer program product storing a computer program, the computer program being loadable into a memory of a processing device of an X-ray device, and including program code sections to cause the processing device to execute the method of claim 9 when the computer program is executed in the processing device.

14. A non-transitory computer readable media storing computer executable instructions for, when executed by a processor, perform the method of claim 9.

15. An X-ray device, comprising:
an X-ray source including a collimator, a radiation source and an actuator configured to move the radiation source with respect to the collimator;
a capturing device including a 3D camera and configured to detect an arrangement of an X-ray detector with respect to the X-ray source,
wherein the capturing device is mechanically connected to the X-ray source and is configured to move together with the X-ray source,
wherein an image generated by the capturing device includes an irradiation area of the X-ray source, and
wherein the image generated by the 3D camera includes the X-ray detector, and
a processor configured to
determine an adjustment for the collimator based on a detected position of the X-ray detector with respect to the X-ray source, and
adjust the collimator based on the adjustment determined for the collimator.

16. An X-ray device, comprising:
an X-ray source including a collimator;
an X-ray detector; and
at least one processor configured to
detect, via a 3D camera, an arrangement of the X-ray detector with respect to the X-ray source by automatically computing, based on an image captured by the 3D camera including the X-ray detector and the X-ray source, at least one of:
a distance between the X-ray detector and the X-ray source, and
an orientation of the X-ray detector with respect to the X-ray source;
automatically determine an adjustment for the collimator based on a position of the X-ray detector determined with respect to the X-ray source; and
automatically adjust the collimator based on the adjustment determined for the collimator.

* * * * *